United States Patent [19]

Hesse

[11] Patent Number: Plant 6,391

[45] Date of Patent: Nov. 15, 1988

[54] KALANCHOE PLANT NAMED CAMPECHE

[75] Inventor: Peter S. Hesse, Bradenton, Fla.

[73] Assignee: Ball Pan Am Plant Co., Parrish, Fla.

[21] Appl. No.: 6,133

[22] Filed: Jan. 23, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named Campeche, characterized by its lemon yellow, partially bicolored flowers, compact growth and floriferous habits, free branching habit, medium size and thick leaves, early flowering, and by its adaptability to production in 10–15 cm pots.

1 Drawing Sheet

1

The present invention relates to a new and distinctive cultivar of Kalanchoe plant, botanically known as Kalanchoe, and referred to by the cultivar name Campeche.

The new cultivar was referred to during the breeding and selection process by the designation K83-683H-Y, and is a product of a planned breeding program. The basic objective of the breeding program was to create a new Kalanchoe cultivar having yellow flowers, compact habit, early flowering, and good keeping quality.

Campeche was originated from a self pollination of the hybrid designated K2-425 in a controlled breeding program in Parrish, Fla. The female, or seed parent was a cultivar named Brandy. The male, or pollen parent of K2-425 was the cultivar Regulus, disclosed in U.S. Plant Pat. No. 4,817.

Campeche was discovered and selected by me as a flowering plant within the progeny of the stated cross in a controlled environment in Parrish, Fla. Asexual reproduction of the new cultivar by stem cuttings, as performed by me at Parrish, Fla., has demonstrated that the combination of characteristics as herein disclosed for the new cultivar are firmly fixed and are retained through successive generations of asexual reproduction.

Campeche has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repeatedly observed and are determined to be basic characteristics of Campeche, which in combination distinguish this Kalanchoe as a new and distinct cultivar:

1. Primarily lemon yellow flower color, with a few yellow-gold flowers produced on each cyme.
2. Compact habit and average growth rate.
3. Freely branching, with shoots formed at every node.
4. Suitable for production in 10–15 cm pots, and flowering in 12–14 weeks using photoperiodic control.
5. Very floriferous, with numerous flowers formed at every node.
6. Responds to B-9 applications to control height.
7. Medium sized leaves that are very thick and persistent.

2

The new cultivar is most similar to the cultivar Fortyniner, with Chart A attached hereto comparing certain important characteristics of each. Campeche is principally distinguished from Fortyniner by its bicolored yellow and yellow-gold flower color, earlier flowering, and larger foliage size.

The accompanying photographic drawing shows a typical specimen plant of the new cultivar. The photograph is in black and white, with several flowers being in color to accurately depict the true flower color.

In the following description, color references are made to The Royal Horticultural Society Colour Chart (R.H.S.), except where general colors or ordinary significance are referred to. Color values were taken under fluorescent light conditions in September in Parrish, Fla.

Botanical classification: Kalanchoe, cv. Campeche.

Parentage: From self pollination of the hybrid K2-425.

Propagation: The new cultivar holds its distinguishing characteristics through successive propagations by leaf cuttings and by division of shoots.

(A) *Type cutting.*—Shoot tip.

(B) *Time to root.*—10–14 days at 21° C.

(C) *Rooting habit.*—Fibrous, many very fine roots.

Plant description:

(A) *Form.*—Upright, short compact growth; scheduling practices can produce small plants in 10 cm pots or larger plants in 15 cm pots.

(B) *Habit of growth.*—Average rate for this type of plant; shoots are formed at every node.

(C) *Foliage description.*—Leaves simple, opposite and ovate with unevenly crenate margins. (1) Size: 5–15 cm long and 5–10 cm wide. (2) Shape: Ovate. (3) Texture: Smooth, waxy and succulent. (4) Margin: Unevenly crenate. (5) Color: Young and mature foliage, top side 147A, under side 147B.

Flowering description:

(A) *Flowering habit.*—Compound dichasial cyme on strong peduncles. Peduncle length depends on growing conditions and B-9 applications. Pedicles up to 5 mm long.

(B) *Natural flowering season.*—Fall, Flowering time under controlled day length at 75° F.–85° F. in summer is 14–15 weeks; in winter at 62° F.–70° F., 11–12 weeks. Flowering time depends on temperature, light intensity and other growing conditions.

(C) *Flower buds.*—Oblong, developing to tubular as petals mature. Sheathed with four green sepals, corolla at maturity about 14 mm. (1) Size: 14 mm. (2) Shape: Oblong. (3) Rate of opening: Normal.

(D) *Flowers borne.*—Compound dichasial cyme on strong peduncles. Peduncle length depends on growing conditions and B-9 applications. Pedicles up to 5 mm long.

(E) *Quantity of flowers.*—Very floriferous, with new buds continuing to develop.

(F) *Petals.*—(1) Shape: Corolla funnel shaped, petal apex abruptly acuminate. (2) Color: Top side when opening, 7B or 12A, fading to 7C or 12B; under side, 7D or 12C. It should be noted that the values 7B and 12A are very close and virtually indistinguishable in terms of readability on the flower petals. (3) Number and size of petals: Four (4), petals 7 mm in diameter, total flower diameter 15–17 mm.

(G) *Reproductive organs.*—(1) Stamens: Eight (8) in number. (a) Anther shape: Flat, elliptical. (b) Filament color: Yellow. (c) Pollen color: Yellow. (2) Pistels (a) Stigma shape: Flat, crystalline. (b) Style color: Greenish-white. (c) Ovaries: 4-celled, 7 mm long, green.

Disease resistance: No known Kalanchoe diseases observed to date.

General observations: Campeche is characterized by its unique lemon yellow flower color, compact and freely branching habit, and medium green foliage. Campeche has an average 12 week flowering response and is adaptable to production in 10–15 cm pots year round.

CHART A

| | Campeche vs. Fortyniner Summer Conditions | |
|---|---|---|
| | Campeche | Fortyniner |
| Mature flower color | 7B and 12A | 8A |
| Flowering plant height | 20 cm | 22 cm |
| Weeks to flower | 13 | 14 |
| Mature leaf width | Up to 9 cm | Up to 8.5 cm |
| Mature leaf length | Up to 15 cm | Up to 13 cm |
| Diameter of Flower | 16 mm | 17 mm |

The plants of Campeche and Fortyniner which were used in this comparison were grown together on the same bench in a greenhouse in Parrish, Fla. The color readings were taken under fluorescent light at 2:00 pm on Sept. 17, 1986.

I claim:

1. A new and distinct cultivar of Kalanchoe plant named Campeche, as described and illustrated, and particularly characterized by its lemon yellow, partially bicolored flowers, compact growth and floriferous habits, free branching habit, medium size and thick leaves, early flowering, and by its adaptability to production in 10–15 cm pots.

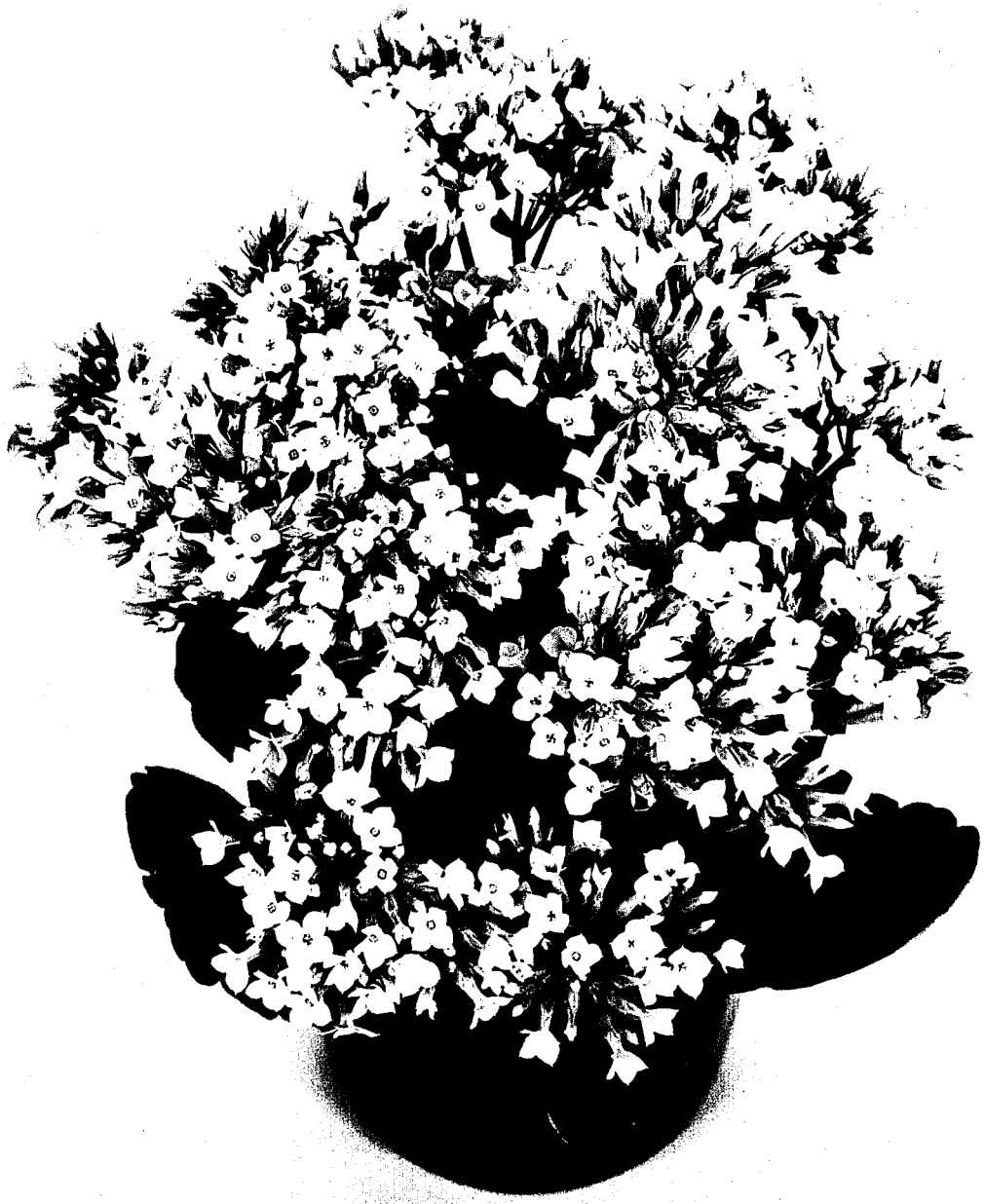

* * * * *